(12) United States Patent
Yamashita et al.

(10) Patent No.: US 9,192,450 B2
(45) Date of Patent: Nov. 24, 2015

(54) DENTAL TREATING APPARATUS WITH HAND PIECE

(71) Applicant: J. Morita Manufacturing Corporation, Kyoto (JP)

(72) Inventors: Seiichiro Yamashita, Kyoto (JP); Tsuyoshi Tanaka, Kyoto (JP); Minoru Imazato, Kyoto (JP); Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 27 days.

(21) Appl. No.: 13/662,604

(22) Filed: Oct. 29, 2012

(65) Prior Publication Data

US 2013/0108978 A1  May 2, 2013

(30) Foreign Application Priority Data

Nov. 1, 2011  (JP) .................................. 2011-239977

(51) Int. Cl.
  *A61C 3/00*  (2006.01)
  *A61C 1/00*  (2006.01)

(52) U.S. Cl.
  CPC .................................. *A61C 1/0015* (2013.01)

(58) Field of Classification Search
  CPC ...... A61C 1/00; A61C 1/0007; A61C 1/0069; A61C 1/0015; A61C 1/0023; A61C 1/003; A61C 1/0038; A61C 1/082; A61C 1/084; A61C 1/085; A61C 1/0053
  USPC ........... 433/27, 102, 29, 72, 32, 215, 224, 98, 433/99
  See application file for complete search history.

(56) References Cited

U.S. PATENT DOCUMENTS

| | | | | |
|---|---|---|---|---|
| 5,042,498 A | * | 8/1991 | Dukes | 600/509 |
| 5,897,315 A | * | 4/1999 | Nakayama et al. | 433/72 |
| 5,902,105 A | * | 5/1999 | Uejima et al. | 433/27 |
| 6,092,722 A | | 7/2000 | Heinrichs et al. | |
| 6,899,538 B2 | * | 5/2005 | Matoba | 433/114 |
| 7,476,101 B2 | * | 1/2009 | McPherson et al. | 433/75 |

(Continued)

FOREIGN PATENT DOCUMENTS

| | | |
|---|---|---|
| DE | 19629646 A1 | 1/1998 |
| EP | 1642547 A1 | 4/2006 |

(Continued)

OTHER PUBLICATIONS

Examination Report w/translation issued in German Patent and Trademark Office Application No. 10 2012 020 790.5, dated Oct. 30, 2013 (11 pages).

(Continued)

*Primary Examiner* — Yogesh Patel
(74) *Attorney, Agent, or Firm* — Osha Liang LLP

(57) ABSTRACT

A dental treating apparatus has a head unit having a holder for drivably holding a cutting tool, a hand piece body connected to the head unit for transmitting power to drive the cutting tool, and a controller for controlling the driving of the cutting tool. The dental treating apparatus further has a conductive body disposed in an inside of the hand piece body for transmitting an electric signal, contact members electrically connecting the cutting tool or the holder with the conductive body, a connection failure detector for applying a predetermined input signal to the conductive body and detecting a connection failure of the contact members based on a response to the input signal obtained via the cutting tool, and a notifier for notifying a user based on the detection result of the connection failure detector.

5 Claims, 10 Drawing Sheets

(56) References Cited

U.S. PATENT DOCUMENTS

| | | | |
|---|---|---|---|
| 2002/0188183 A1* | 12/2002 | Kusakabe et al. | 600/300 |
| 2004/0004492 A1* | 1/2004 | Hsu | 324/765 |
| 2005/0143724 A1 | 6/2005 | El-Galley et al. | |
| 2006/0068356 A1 | 3/2006 | Eibl et al. | |
| 2009/0047616 A1* | 2/2009 | Eibl et al. | 433/27 |
| 2010/0036535 A1 | 2/2010 | Feine et al. | |

FOREIGN PATENT DOCUMENTS

| | | |
|---|---|---|
| JP | 3213480 B2 | 10/2001 |
| JP | 3213539 B2 | 10/2001 |
| JP | 4638796 B2 | 2/2011 |

OTHER PUBLICATIONS

English Patent Abstract of JP 3213480, from esp@cenet, Publication Date: Oct. 2, 2001 (1 Page).

English Patent Abstract of JP 3213539, from esp@cenet, Publication Date: Oct. 2, 2001 (1 Page).

English Patent Abstract of JP 4638796, from esp@cenet, Publication Date: Feb. 23, 2011 (1 Page).

* cited by examiner (a)

(b)

DENTAL TREATING APPARATUS WITH HAND PIECE

BACKGROUND OF THE INVENTION

1. Field of the Invention

The present invention relates to a dental treating apparatus with a hand piece, more specifically, to a dental treating apparatus having an electrical contact with respect to a cutting tool for cutting and enlarging an inner wall of a root canal of a tooth or a holder for holding the cutting tool.

2. Description of the Background Art

As for a dental treating apparatus with a hand piece, a dental hand piece for treating a root canal used for treating a root canal by cutting and enlarging the root canal of a tooth and for measuring a length of the root canal is provided. For example, following patent documents disclose specific examples of the hand piece for treating the dental root canal.

In a dental hand piece for treating a root canal disclosed in U.S. Pat. No. 3,213,480, an installation unit of a head unit to be installed on a hand piece body is configured by a conductive member. Accordingly, by installing the head unit on the hand piece body in the hand piece for treating the dental root canal as disclosed in U.S. Pat. No. 3,213,480, the installation unit of the head unit is electrically connected to a conductive member (such as a driving and transferring mechanism) configuring a root canal length measuring circuit in the hand piece body.

Also, in the dental hand piece for treating the root canal as disclosed in U.S. Pat. No. 3,213,480, the installation unit of the head unit is electrically connected with a tool holding mechanism for mounting the cutting tool on the head unit via a brush mechanism provided in the installation unit of the head unit. Thereby, the dental hand piece for treating the root canal as disclosed in U.S. Pat. No. 3,213,480 can configure one of signal transmitting circuits for measuring a root canal length to the cutting tool (as shown in FIGS. 2 and 3 of U.S. Pat. No. 3,213,480).

Further, in a dental hand piece for treating a root canal as disclosed in U.S. Pat. No. 3,213,539, a terminal pin connected to a lead in a hand piece body, a contact plug, and a contact jack are disposed in a head unit. In the dental hand piece for treating the root canal as disclosed in U.S. Pat. No. 3,213,539, a contact is attached to the contact jack via a contact plate on a lower surface of the head unit. Here, the contact is configured to be rotated in a vertical direction or a horizontal direction, or slid to contact with a cutting tool. Thereby, the dental hand piece for treating the root canal as disclosed in U.S. Pat. No. 3,213,539 can configure one of signal transmitting circuits for measuring a root canal length to the cutting tool.

Moreover, in a dental hand piece for treating a root canal as disclosed in U.S. Pat. No. 4,638,796, a hand piece body is configured by conductive member, and an insulated and coated conductive wire for transmitting a root canal length measurement signal is disposed in a hand piece where a tip end of the conductive wire is bifurcated. Also, in the dental hand piece for treating the root canal as disclosed in U.S. Pat. No. 4,638,796, one of the bifurcated conductive wire is caused to contact with a head unit shaft member (a tool holder) via contact means and the other is connected to a U-shaped elastic wire. The U-shaped elastic wire is configured to contact with a tool installed on the tool holder.

In the dental hand piece for treating the root canal as disclosed in U.S. Pat. No. 3,213,480, a brush mechanism as an electrical contact is provided in the installation unit of the head unit to sandwich a rotation body (a rotor) as the tool holding mechanism such that the hand piece configures one of the signal transmitting circuits to the cutting tool for measuring the root canal length. In the dental hand piece for treating the root canal as disclosed in U.S. Pat. No. 3,213,480, however, there is a problem in that even if connection error occurs between the rotor and the brush mechanism since the brush mechanism wears out due to receiving repeated rotations of the rotor, it cannot be externally determined whether or not the connection error occurs between the rotor and the brush mechanism.

Also, in the dental hand piece for treating the root canal as disclosed in U.S. Pat. No. 3,213,480, when the connection failure occurs between the rotor and the brush mechanism, a display of a measurement result of a root canal length changes or the display blinks on and off in some cases. In the dental hand piece for treating the root canal as disclosed in U.S. Pat. No. 3,213,480, however, even if a failure occurs in the signal transmitting circuit itself for measuring the root canal length, the display of the measurement result of the root canal length changes or the display blinks on and off in some cases in a similar manner. Accordingly, it is difficult to determine whether the connection error occurs between the rotor and the brush mechanism or the failure occurs in the signal transmitting circuit itself for measuring the root canal length from merely the display of the measurement result of the root canal length.

In the dental hand piece for treating the root canal as disclosed in U.S. Pat. No. 3,213,539, since the contact contacts with the cutting tool on the lower surface of the head unit, an electrical contact point between the contact and the cutting tool is externally exposed. Accordingly, in the dental hand piece for treating the root canal as disclosed in U.S. Pat. No. 3,213,539, even if the contact wears out due to receiving the repeated rotations of the cutting tool to cause a connection failure between the contact and the cutting tool, the wear of the contact can be easily determined by viewing an appearance. It should be noted that it is conceivable that there are some cases where the connection failure between the contact and the cutting tool cannot be determined by merely viewing the appearance when a film of an insulator is formed on a surface of the contact to cause a connection failure between the contact and the cutting tool, for example.

In the dental hand piece for treating the root canal as disclosed in U.S. Pat. No. 4,638,796, the contact means connected to the one of the bifurcated conductive wire is configured to contact with the tool holder in the head unit and the U-shaped elastic wire connected to the other of the bifurcated conductive wire is configured to contact with the tool outside the head unit. In the dental hand piece for treating the root canal as disclosed in U.S. Pat. No. 4,638,796, however, there is a problem in that even if connection error occurs between the tool holder and the contact means since the contact means wears out due to receiving repeated rotations of the tool holder, it cannot be externally determined whether or not the connection error occurs between the tool holder and the contact means.

SUMMARY OF THE INVENTION

The present invention provides a dental treating apparatus that can easily determine whether or not a connection failure occurs in a contact member electrically connecting a cutting tool or a holder holding the cutting tool with a conductive body provided in an inside of a hand piece body.

The dental treating apparatus according to the present invention includes a head unit having a holder drivably holding a cutting tool, a hand piece body connected to the head unit for transmitting power to drive the cutting tool, and a controller for controlling the driving of the cutting tool. The dental treating apparatus further includes a conductive body disposed in an inside of the hand piece body for transmitting an electric signal, contact members electrically connecting the cutting tool or the holder with the conductive body, a connection failure detector for applying a predetermined input signal to the conductive body and detecting a connection failure of the contact members based on a response to the input signal obtained via the cutting tool, and a notifier for notifying a user based on the detection result by the connection failure detector.

Since the dental treating apparatus according to the present invention detects the connection failure of the contact members based on the response to the input signal by the connection failure detector, the connection failure due to wear of the contact members can be easily detected even in a case where the contact members are provided out of the head unit as well as a case where the contact members are provided in the head unit such that an appearance cannot be viewed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention are described with reference to the drawings.

(First Embodiment)

A dental treating apparatus according to a first embodiment of the present invention is a root canal treating device including a root canal enlarging and root canal length measuring system into which a dental hand piece for treatment on a root canal is incorporated. The dental treatment apparatus according to the present invention is, however, not limited to the root canal treating device, and can be applied to a dental treating apparatus with a similar configuration.

Figure 1:
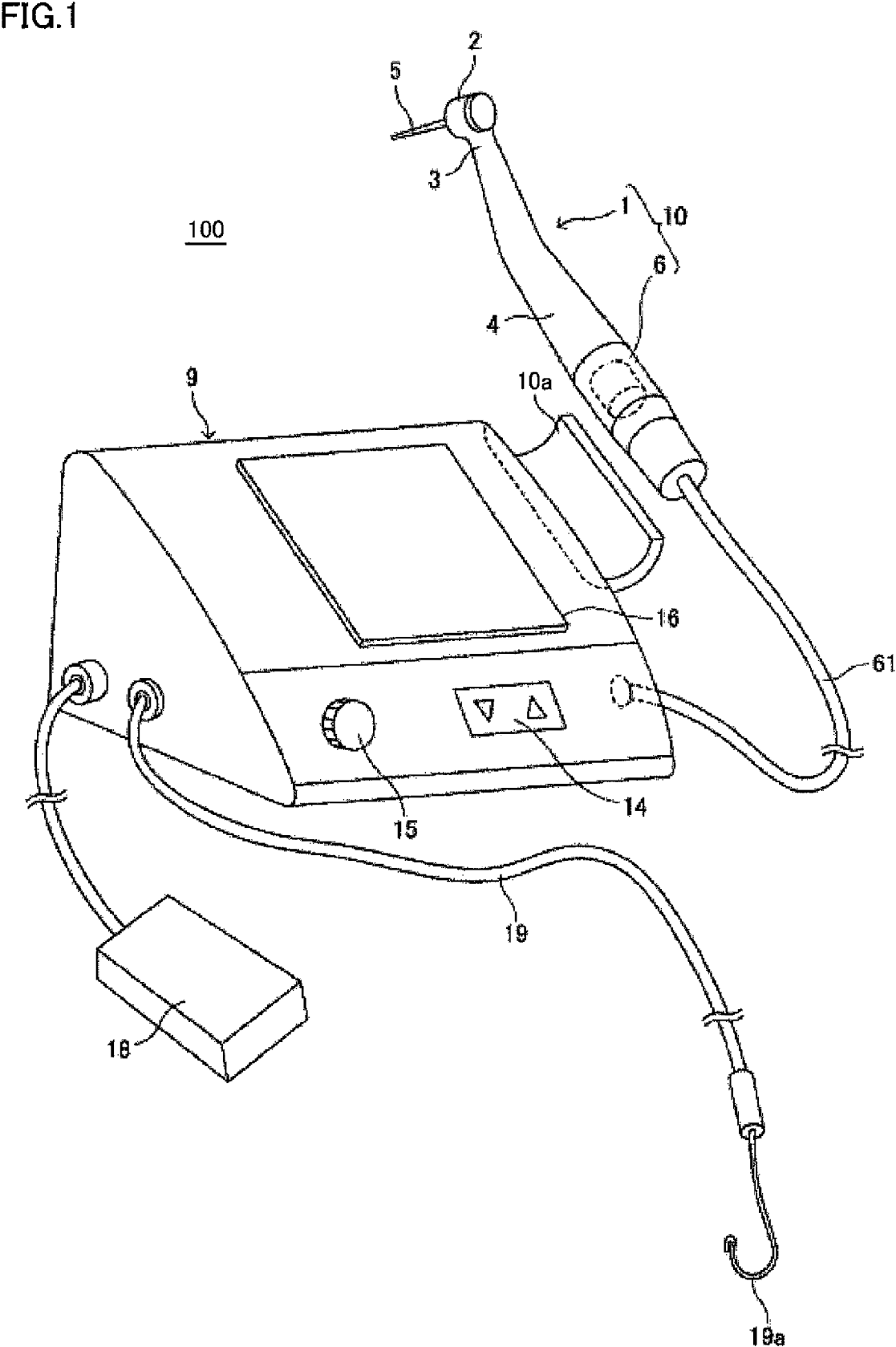
FIG. 1 is a schematic diagram showing an appearance of a configuration of the root canal treating device according to a first embodiment of the present invention.
Figure 2:
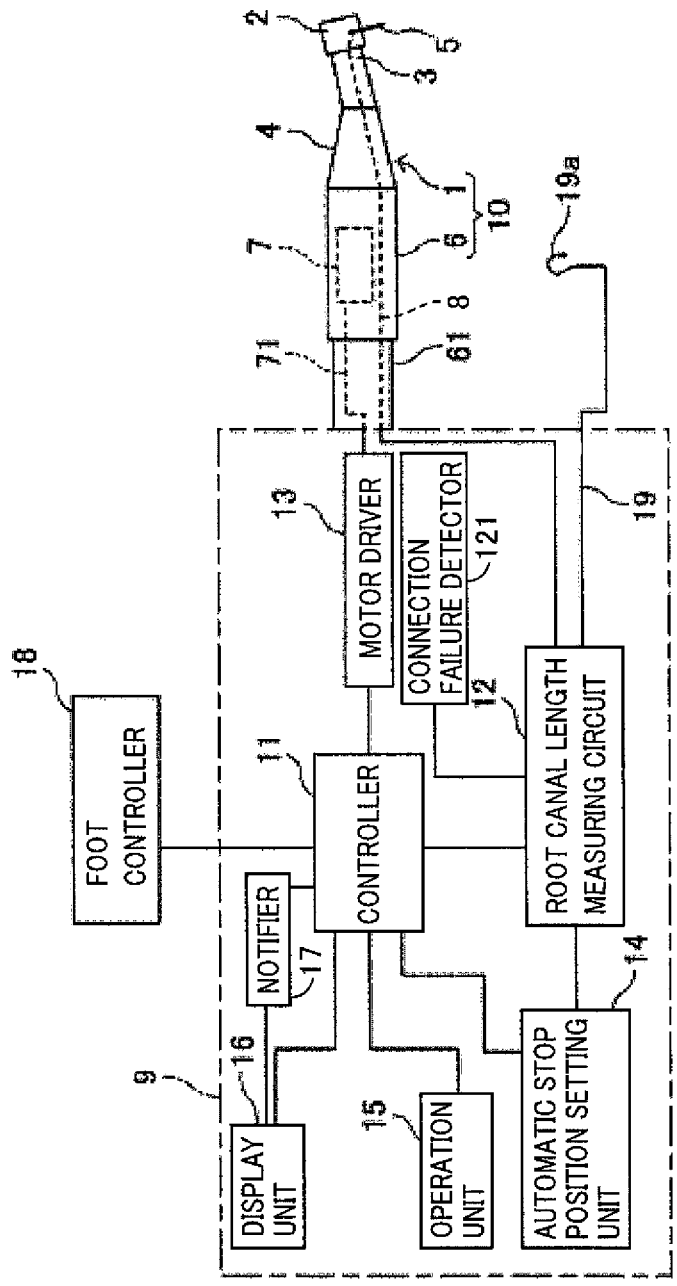
FIG. 2 is a block diagram showing a configuration of functions of the root canal treating device according to the first embodiment of the present invention.

FIG. 1 is a schematic diagram showing an appearance of a configuration of the root canal treating device according to the first embodiment of the present invention. FIG. 2 is a block diagram showing a configuration of functions of the root canal treating device according to the first embodiment of the present invention. A root canal treating device 100 as shown in FIG. 1 includes a hand piece 1, a motor unit 6, a control box 9 for treating dental root canal.

Hand piece 1 for treating the dental root canal includes a head unit 2, a neck unit 3 with a small diameter connected to head unit 2, and a grip 4 connected to neck unit 3 and gripped by a hand or fingers. Further, to a base unit of grip 4, motor unit 6 is detachably connected for rotating and driving a cutting tool 5 to be installed on head unit 2. A dental instrument 10 is configured with hand piece 1 and motor unit 6 coupled to each other.

As shown in FIG. 2, a micro motor 7 is embedded in motor unit 6 that is connected to control box 9 through a hose 61 containing therein a power supply lead 71 for supplying power to micro motor 7, a signal lead 8 for transmitting a signal to a root canal length measuring signal circuit to be described below, and the like. Here, signal lead 8 is a part of a conductive body for transmitting an electric signal, signal lead 8 being electrically connected to cutting tool 5 through motor unit 6 and hand piece 1 as described below. It is also noted that cutting tool 5 is one of electrodes of the root canal length measuring circuit as described below.

Control box 9 includes a controller 11, a root canal length measuring circuit 12, a motor driver 13, an automatic stop position setting unit 14, an operation unit 15, a display unit 16, and the like. As shown in FIG. 1, it should be noted that control box 9 is provided with a holder 10a holding instrument 10 when instrument 10 is not used, at a lateral part of a body. Also, a foot controller 18 is connected to control box 9. Further, control box 9 is connected to a lead 19 through which control box 9 is electrically connected to root canal length measuring circuit 12. Lead 19 may be in a form that is bifurcated at an intermediate portion of hose 61. A mouth electrode 19a hung on a lip of a patient is attached to a tip end of lead 19 in an electrically conductive state. It should be noted that mouth electrode 19a is the other one of the electrodes of root canal length measuring circuit 12.

A primary part of controller 11 for controlling the whole system for enlarging the root canal and measuring the root canal length is configured by a microcomputer. Root canal length measuring circuit 12, motor driver 13, automatic stop position setting unit 14, controller 15, display unit 16, a notifier 17, and foot controller 18 are connected to control unit 11.

Root canal length measuring circuit 12 configures a closed circuit with cutting tool 5 inserted in the root canal of the tooth as one electrode and mouth electrode 19*a* hung on the lip of the patient as the other electrode. Root canal length measuring circuit 12 can measure a distance (root canal length) from an apical position of the tooth to a tip end of cutting tool 5 by applying voltage between cutting tool 5 and mouth electrode 19*a* and measuring impedance between cutting tool 5 and mouth electrode 19*a*. It should be noted that a method for electrically measuring the root canal length by measuring the impedance between cutting tool 5 and mouth electrode 19*a* is publicly known and all publicly-known methods for electrically measuring the root canal length can be applied to root canal treating device 100 according to the first embodiment of the present invention.

Automatic stop position setting unit 14 to be described below and connection failure detector 121 are connected to root canal length measuring circuit 12. Connection failure detector 121 applies an input signal to the conductive body disposed from root canal length measuring circuit 12 to the inside of hand piece 1 to obtain a response to the input signal via cutting tool 5. Connection failure detector 121 then detects a connection failure of contact members electrically connecting cutting tool 5 or a holder holding cutting tool 5 with signal lead 8 based on the response to the input signal obtained via cutting tool 5.

Motor driver 13 is connected to micro motor 7 via power supply lead 71 and controls the power supplied to micro motor 7 based on a control signal from controller 11. Motor driver 13 can control the number of rotations of micro motor 7, namely the number of rotations of cutting tool 5 by controlling the power supplied to micro motor 7.

Automatic stop setting unit 14 sets a position in the root canal to be a reference in advance while viewing display unit 16 upon performing enlarging treatment on the root canal of the tooth with rotating cutting tool 5 so as to automatically stop or reverse the rotation of cutting tool 5 when the tip end of cutting tool 5 reaches the set position. Selection whether or not a control such as the automatic stop is performed can be made by operation unit 15.

Operation unit 15 selects whether or not the control such as the automatic stop is performed as well as whether or not the root canal length is measured.

Display unit 16 displays a position of the tip end of cutting tool 5 in the root canal and the number of rotations of cutting tool 5 as described below. Also, display unit 16 can display information for notifier 17 to notify a user of the connection failure of the contact members based on the detection result of connection failure detector 121.

Notifier 17 notifies the user by light, sound, vibration, and the like of the connection failure of the contact members electrically connecting cutting tool 5 with signal lead 8 based on the detection result of connection failure detector 121. Specifically, notifier 17 includes an LED (Light Emitting Diode), a speaker, an oscillator, and the like according to the need to notify the user of the connection failure of the contact members. Also, notifier 17 need not include the LED, the speaker, the oscillator and the like separately if display unit 16 can display information for notifying the user of the connection failure of the contact members based on the detection result of connection failure detector 121.

Foot controller 18 is an operation unit for performing rotation control on cutting tool 5 by micro motor 7 by a stepping operation. It should be noted that the rotation control on cutting tool 5 by micro motor 7 is not limited to foot controller 18, namely, an operation switch (not shown) is provided in grip 4 of hand piece 1 to perform the rotation control by this operation switch and foot controller 18. Also, for example, in a state where the stepping operation via foot controller 18 is performed, the rotation of cutting tool 5 may be started by detecting, using root canal length measuring circuit 12, that cutting tool 5 is inserted into the root canal.

It should be noted that a configuration is disclosed in that control box 9 of root canal treating device 100 is put on a tray table or a side table installed on a lateral part of a dental treatment table and used, the present invention is not limited to such a configuration but can include a configuration in that control box 9 is incorporated into the tray table or the side table. Also, a configuration is disclosed in that hand piece 1 is coupled to control box 9 via hose 61, the present invention is not limited to such a configuration but can be configured as a cordless type. Specifically, hand piece 1 of the cordless type is configured such that a battery pack, a micro motor, and a control system corresponding to control box 9 are incorporated into grip 4, each type of operation units is disposed on a surface of grip 4, and lead 19 for mouth electrode 19*a* is led from grip 4.

Figure 3:
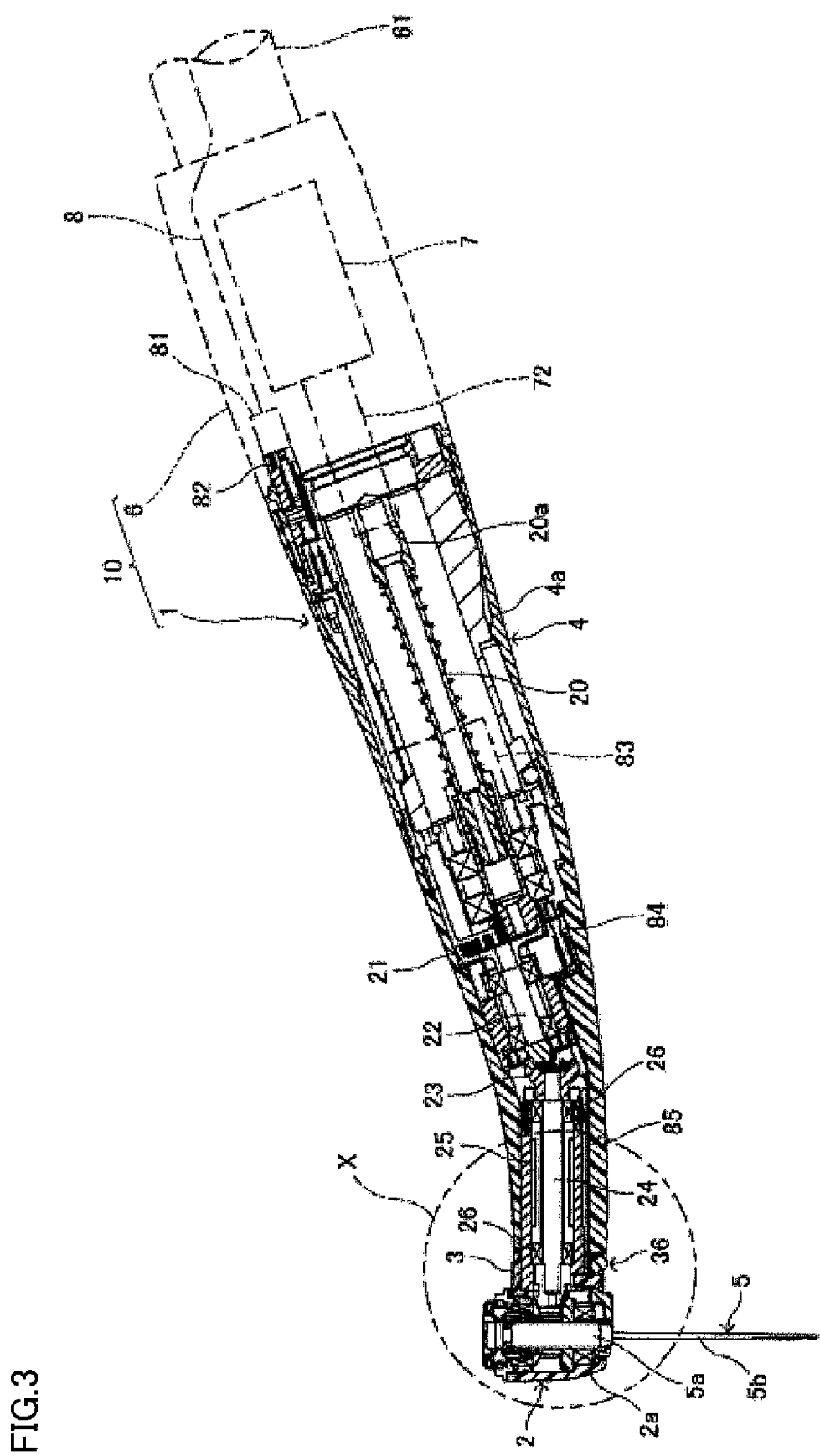
FIG. 3 is a cross-sectional view illustrating the configuration of the hand piece according to the first embodiment of the present invention.
Figure 4:
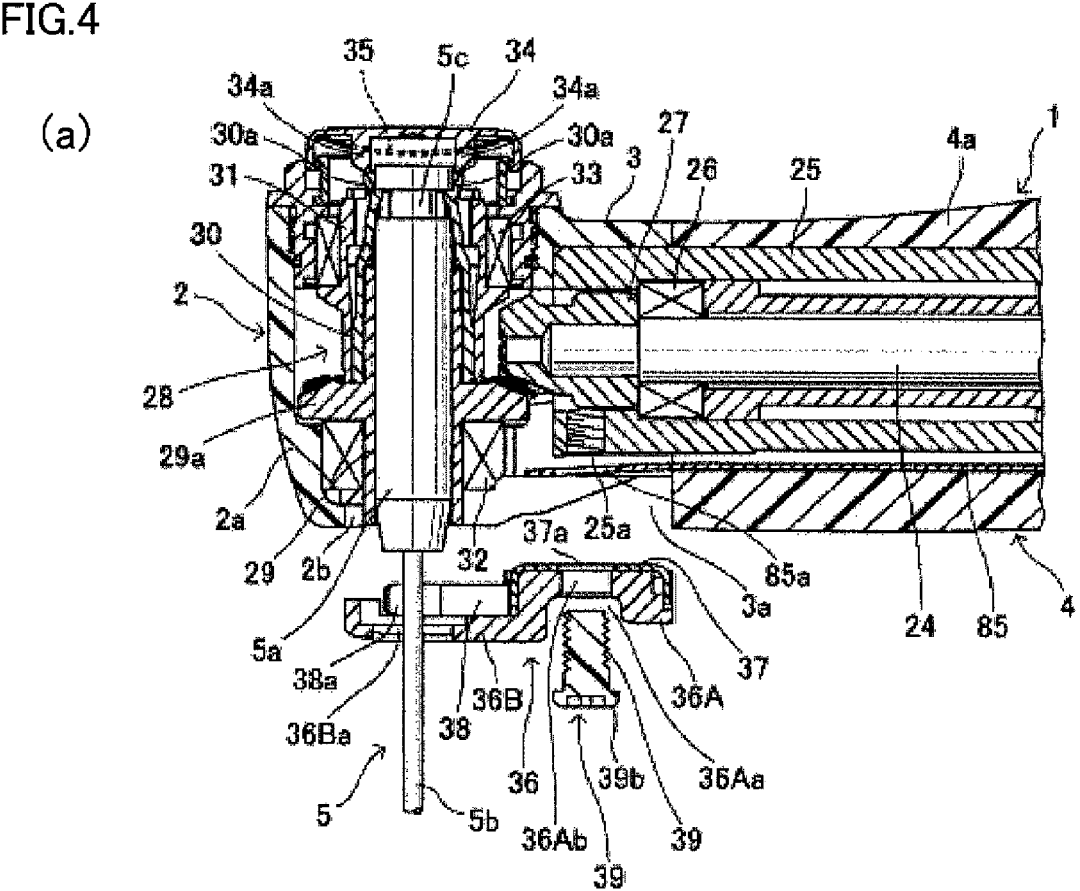
FIG. 4 is a cross-sectional view illustrating the configuration of a tip end of the hand piece according to the first embodiment of the present invention.
Figure 4:
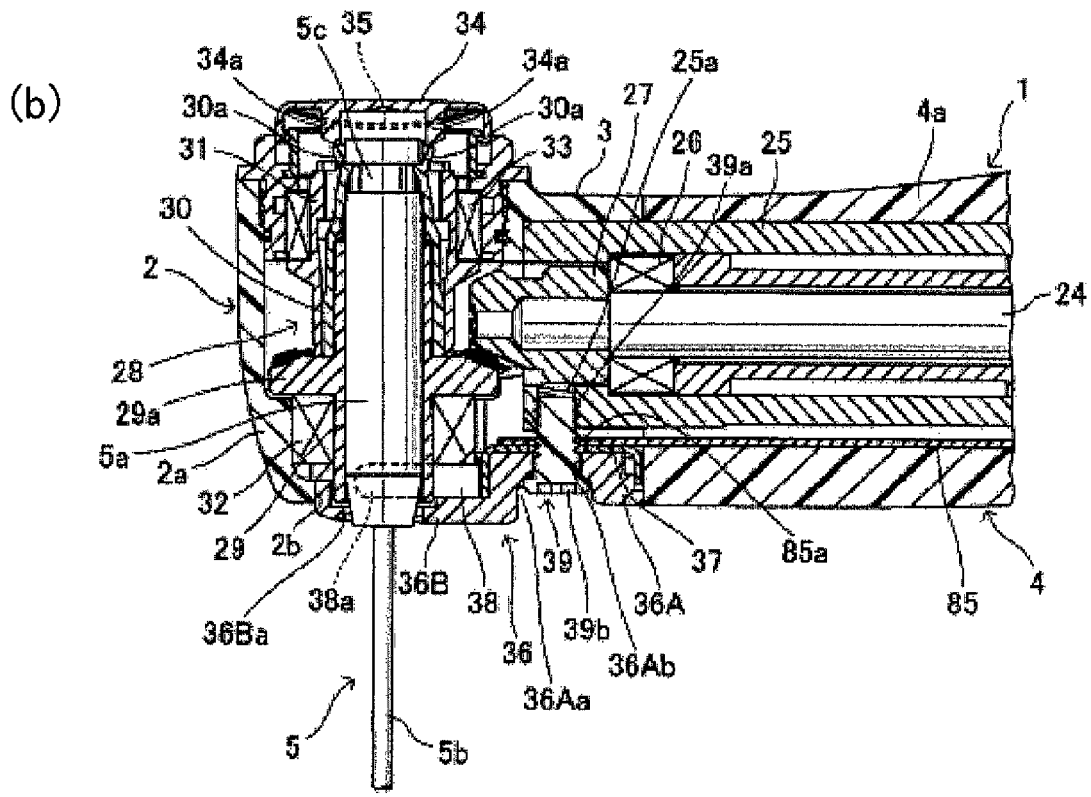

Next, a configuration of hand piece 1 is described in more details. FIG. 3 is a cross-sectional view illustrating the configuration of hand piece 1 according to the first embodiment of the present invention. FIG. 4 is a cross-sectional view illustrating the configuration of a tip end of hand piece 1 according to the first embodiment of the present invention. A front half part of hand piece 1 as shown in FIG. 4 is shaped as contra-angle in which a housing 4*a* of grip 4 formed by a molded body of a synthetic resin and a head housing 2*a* formed by a molded body of a synthetic resin via neck unit 3 are provided in series. In housing 4*a* of grip 4, a first drive transfer shaft 20 is axially rotatably embedded that is coupled to an output shaft 72 of micro motor 7 via a coupling unit 20*a* when motor unit 6 is connected to a base of grip 4. A second drive transfer shaft 22 is axially rotatably coupled to a tip end of first drive transfer shaft 20 via a first reduction gear mechanism 21 in series, and in a portion reaching a neck unit 3, a third drive transfer shaft 24 is axially rotatably coupled to second drive transfer shaft 22 via a second reduction gear mechanism 23 as a flex part. A socket 81 connected to signal lead 8 is provided at a tip end of motor unit 6, and a plug 82 inserted and connected to socket 81 is provided at the base of grip 4. A lead 83 provided from plug 82 through housing 4*a* of grip 4 is coupled to a strip-shaped conductive body 85 that reaches neck unit 3 via a connector 84 including the socket and a pin in an electrically conductive state. As shown in FIG. 4*a*, in a lower surface of neck unit 3, a concave part 3*a* is provided toward an axis side from a peripheral surface of neck unit 3 where a tip end of conductive body 85 is exposed to face this concave part 3*a*. It should be noted that FIG. 4(*a*) is a cross-sectional view of the enlarged tip end of hand piece 1 shown in a range X of FIG. 3 in a state before a cover member 36 is fit onto and installed on the tip end of hand piece 1. It should be noted that FIG. 4(*b*) is a cross-sectional view of the enlarged tip end of hand piece 1 shown in the range X of FIG. 3 in a state after cover member 36 is fit onto and installed on the tip end of hand piece 1.

Third drive transfer shaft 24 is axially rotatably supported, via a bearing 26, in a metal sleeve 25 integrally fit into housing 4*a* of grip 4 and a bevel gear 27 is fixed on the tip end. Conductive body 85 is insulated with respect to sleeve 25 via a space. Further, a female thread 25*a* is formed in a portion of sleeve 25 corresponding to concave part 3*a*. In a head housing 2*a* of head unit 2, a tool holding mechanism 28 is embedded for holding cutting tool 5 rotatably about an axis perpendicular to an axis of third drive transfer shaft 24. The tool holding mechanism 28 includes a cylindrical hollow rotor (tool holder) 29 formed of conductive member including a gear 29a engaged with bevel gear 27, a chuck member 30 integrally fit onto rotor 29, and a cylindrical rotor cover member 31 integrally fit onto chuck member 30. Rotor 29, chuck member 30, and rotor cover member 31 are axially rotatably and integrally supported by head housing 2a via bearings 32, 33.

Cutting tool 5 referred to as a file or a reamer is configured by a shank 5a insertably fit into an inner cylindrical unit of rotor 29 in a sealing manner, and a pin-shaped cutting operation unit 5b integrally pressed fit into shank 5a. Cutting tool 5 as a whole is formed of a conductive member. On an upper end of cutting tool 5, a latch concave part 5c is formed for elastically latching a pair of chuck claws 30a, 30a formed on chuck member 30. Hereinafter, with reference to the drawing as shown in FIG. 4, terms "upper" and "lower" are used for showing an upper side and a lower side on the drawing respectively. As cutting tool 5 is inserted into an inner cylinder of rotor 29 via shank 5a, chuck claws 30a, 30b are elastically fit into latch concave part 5c to be latched, thereby preventing cutting tool 5 from being pulled out of rotor 29. Further, in the upper end of cutting tool 5, a D-shaped cut part (not shown) is formed, and in a receiving part (not shown) with a shape corresponding to a shape of the D-shaped cut part is formed in rotor cover member 31. In a state where cutting tool 5 is inserted into rotor 29 so that cutting tool 5 cannot be pulled out of rotor 29, the D-shaped cut part is received by the receiving part and cutting tool 5 is in a state that can be axially rotated together with rotor 29. At this moment, cutting tool 5 is fit into rotor 29 in a sealing manner so that cutting tool 5 and rotor 29 are in electrically conductive state.

An upper end of head housing 2a opens. A latch release button 34 is attached to this opening as a lid body. An operation cylinder 34a protrudes in a lower direction from a lower surface of this latch release button 34 where latch release button 34 is normally biased in an upper direction by a spring member 35 and installed in a state where latch release button 34 is prevented from being pulled out in the upper direction. Then, by pressing latch release button 34 against biasing force of spring member 35, a lower end of operation cylinder 34a protruding from the lower surface of latch release button 34 operates to push and extend chuck claws 30a, 30a. Thereby, latching of chuck claws 30a, 30a with respect to latch concave part 5c is released so that cutting tool 5 can be pulled out of rotor 29. A lower end of head housing 2a is roundly cut out to form a cutout 2b to expose a peripheral portion of a lower end of rotor 29 such that this cutout 2b is formed continuous to concave part 3a formed in the lower surface of neck unit 3.

Cover member 36 is fit into and installed on continuous concave part 3a and cutout 2b. The cover member 36 formed by a non-conductive metal member or a synthetic resin member is shaped to be fit into concave part 3a and cutout 2b in a state where cover member 36 contacts with an inner peripheral surface of concave part 3a and cutout 2b in a sealing manner. The cover member 36 is formed by a first part 36A fit into concave part 3a and a second part 36B fit into cutout 2b, so that first and second parts 36A and 36B are integrally formed in a stepped shape. A contact piece 37 formed of a plate conductive member is fixed onto an upper surface of first part 36A in a surface contacting state, and a pair of electrode pieces 38, 38 as sandwiching pieces having arc-shaped parts 38a, 38a integrally contacting with contact piece 37 and facing to each other are formed over an upper surface of second part 36B. Electrode pieces 38, 38 are formed such that plate surfaces thereof are perpendicular to the upper surface of second part 36B, and a diameter of a virtual circle defined by an inner peripheral surface of arc-shaped parts 38a, 38a of electrode pieces 38, 38 is set slightly smaller than an outer diameter of a lower end of rotor 29.

A groove concave part 36Aa opening in a lower direction is formed in a lower surface of first part 36A of cover member 36, and a round hole 36Ab is formed in a substantially central portion of groove concave part 36Aa. Further, in a substantially central portion of second part 3613, a round hole 36Ba is formed in a concentric manner with respect to the virtual circle defined by the inner peripheral surface of arc-shaped parts 38a, 38a. Round hole 36Ab formed in first part 36A is provided through which a stopper 39 is inserted, and a concentric through hole 37a is also provided at a corresponding position in contact piece 37. Moreover, a through hole 85a is also formed at a position corresponding to a female thread 25a formed on sleeve 25 in conductive body 85. Stopper 39 has a male thread 39a to be passed through round hole 36Ab, through hole 37a and through hole 85a where a head unit 39b is screwed by a tool such as a driver such that male thread 39a engages with female thread 25a. Thereby, cover member 36 fit into concave part 3a and cutout 2b is fixed to be installed on sleeve 25. As shown in FIG. 4(b), in this fixed state, head unit 39b of stopper 39 is stored in groove concave part 36Aa substantially without protruding therefrom, and first part 36A is also substantially stored in concave part 3a to be in a state forming a part of a contour of neck unit 3 in the vicinity of concave part 3a. Furthermore, contact piece 37 elastically contacts with a tip end of conductive body 85 to press the tip end upwards so that both of contact piece 37 and conductive body 85 are in an electrically conductive state. In order to ensure this elastically contacted state, it is desirable that a portion (tip end) of conductive body 85 facing concave part 3a is formed as a free end to have a flexed or curved shape hung slightly in a lower direction in concave part 3a.

A diameter of round hole 36Ba formed in second part 36B of cover member 36 is slightly greater than an external diameter of shank 5a of cutting tool 5. Installation of first part 36A fit into concave part 3a is made simultaneously with second part 36B fit into cutout 2b. At this moment, the pair of sandwiching electrode pieces 38, 38 are pressed to be extended so that arc-shaped parts 38a, 38a elastically contact with an outer peripheral surface of rotor 29 by sandwiching the outer peripheral surface of a lower end of rotor 29. Thereby, an electrically conductive state of electrode pieces 38, 38, and rotor 29 is achieved. In particular, according to a size relationship between the diameter of the virtual circle defined by the inner peripheral surface of arc-shaped parts 38a, 38a of electrode pieces 38, 38 and the outer diameter of rotor 29 at the lower end, the electrically conductive state of both of electrode pieces 38, 38 and rotor 29 elastically contacted with each other is stably maintained. Although the pair of sandwiching electrode pieces 38, 38 are illustrated as the electrode pieces, a single tongue-shaped piece may be elastically contacted with rotor 29.

In a state where cover member 36 is fit into and installed on concave part 3a and cutout 2b, cutting tool 5 is passed through round hole 36Ba of second part 36B to be inserted into the inner cylinder of rotor 29 and held by tool holding mechanism 28 via chuck member 30, or the like. In this held state, rotor 29 and cutting tool 5 can be integrally and axially rotated and rotation power of micro motor 7 is transferred to cutting tool 5 to be rotated so as to perform enlarging treatment on the root canal of the tooth by cutting operation unit 5b of cutting tool 5. At this moment, sandwiching electrode pieces 38, 38 slidably contact with an outer peripheral surface of rotor 29 as a brush contact. Further, cutting tool 5 is integrally fit into rotor 29 in a sealing state so that rotor 29 is in an electrically conductive state with respect to lead 8 via electrode pieces 38, 38, contact piece 37, conductive body 85, and lead 83, and the like. Accordingly, in a state where cutting tool 5 is inserted into the root canal of the tooth as one of the electrodes for measuring the root canal length and mouth electrode 19a is hung on the lip of the patient as the other one of the electrodes, root canal length measuring circuit 12 as shown in FIG. 2 is driven so as to measure the root canal length.

In hand piece 1, as described above, sandwiching electrode pieces 38, 38 slidably contact with the outer peripheral surface of rotor 29 as the brush contact so that rotor 29 and electrode pieces 38, 38 are electrically connected to each other. Since rotor 29 and cutting tool 5 can be integrally and axially rotated, contact between rotor 29 and electrode pieces 38, 38 may wear out to cause a connection failure of electrode pieces 38, 38 as contact members. Since electrode pieces 38, 38 as the contact members are covered by cover member 36, however, it is difficult to externally view the wear of electrode pieces 38, 38. Accordingly, root canal treating device 100 according to the first embodiment of the present invention detects a connection failure at the contact between rotor 29 and cutting tool 5 to notify a user of the detection.

Figure 5:
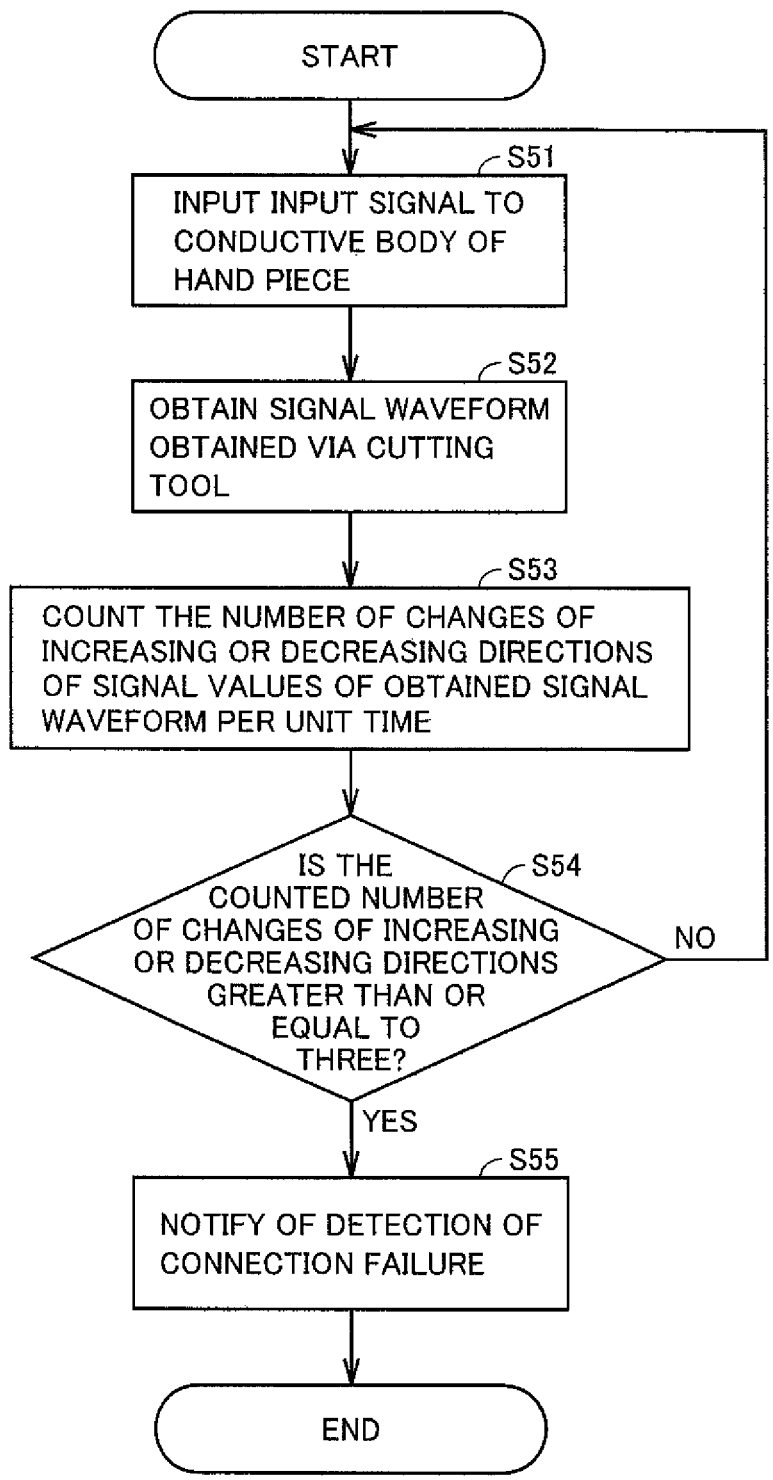
FIG. 5 is a flowchart showing operations of the root canal treating device according to the first embodiment of the present invention.

Specifically, operations of connection failure detector 121 of root canal treating device 100 according to the first embodiment of the present invention are disclosed. FIG. 5 is a flowchart showing the operations of root canal treating device 100 according to the first embodiment of the present invention.

First, connection failure detector 121 applies an input signal for measuring the root canal length from root canal length measuring circuit 12, i.e., an input signal of frequency of 8 kHz to conductive body 85 of hand piece 1 (step S51). In order to detect the connection failure, a signal different from the input signal for measuring the root canal length may be generated and applied to conductive body 85 of hand piece 1, but it is necessary to provide a configuration for generating the signal separately. Accordingly, the configuration may be simplified much more when the input signal for measuring the root canal length is used.

Figure 6:
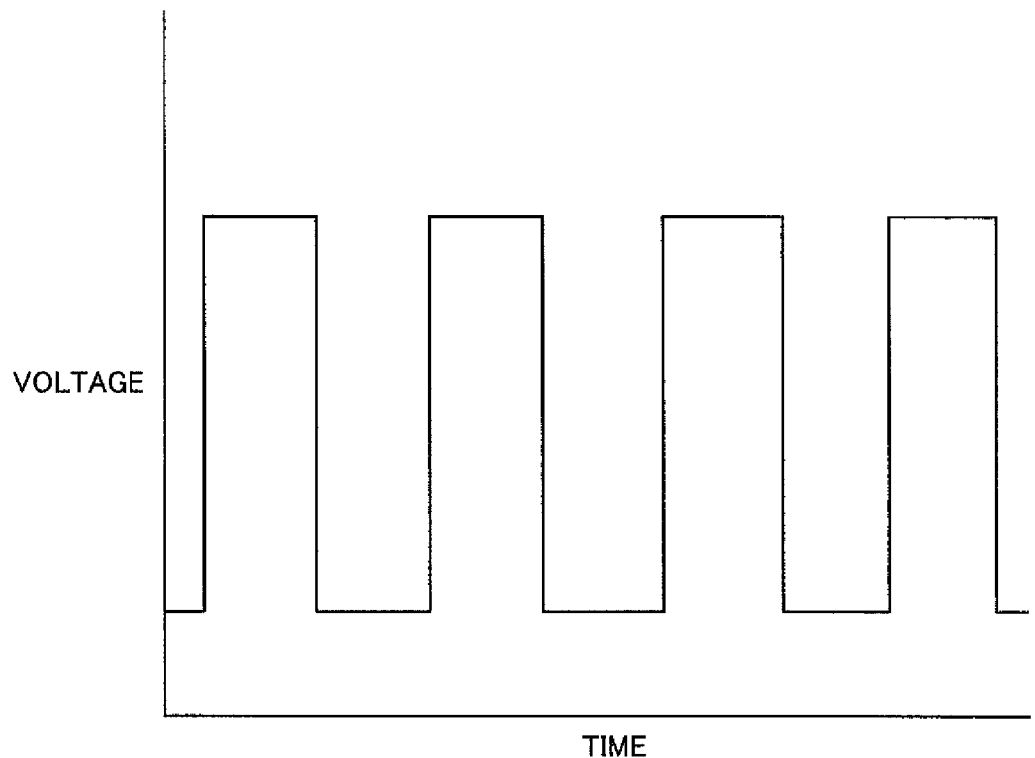
FIG. 6 is a waveform chart showing a waveform of an input signal to be applied to a conductive body of the hand piece according to the first embodiment of the present invention.

Here, FIG. 6 is a waveform chart showing a waveform of the input signal to be applied to conductive body 85 of hand piece 1 according to the first embodiment of the present invention. The input signal as shown in FIG. 6 is of a rectangular wave of a frequency of 8 kHz for measuring the root canal length. It should be noted that a horizontal axis in FIG. 6 shows time, while a vertical axis shows voltage.

Next, connection failure detector 121 applies an input signal to conductive body 85 of hand piece 1 to obtain a signal waveform obtained via cutting tool 5 (step S52). The input signal applied to conductive body 85 of hand piece 1 flows from conductive body 85 to cutting tool 5 via contact piece 37, electrode pieces 38, 38, and rotor 29. Accordingly, in connection failure detector 121, when the connection failure occurs in electrode pieces 38, 38 as the contact members, a signal waveform (a response to the input signal) obtained via cutting tool 5 with respect to the input signal applied to conductive body 85 of hand piece 1 changes. In practice, the waveform obtained via cutting tool 5 is a waveform obtained from the signal input from mouth electrode 19a to connection failure detector 121.

Next, connection failure detector 121 counts the number of changes of increasing or decreasing directions of signal values of the obtained signal waveform per unit time (step S53). Specifically, connection failure detector 121 regards a half cycle of the rectangular wave of input signal as unit time, and counts the number of changes of greater than or equal to 10% of signal values with respect to an average value of the signal values per the unit time from an increasing (decreasing) direction to a decreasing (increasing) direction. It should be noted that connection failure detector 121 regards the change of increasing (decreasing) direction of, for example, greater than or equal to 10% of the signal values with respect to the average value of the signal values per the unit time as reference for determination to exclude a change of signal values due to noise, however, the present invention is not limited to this.

Figure 7:
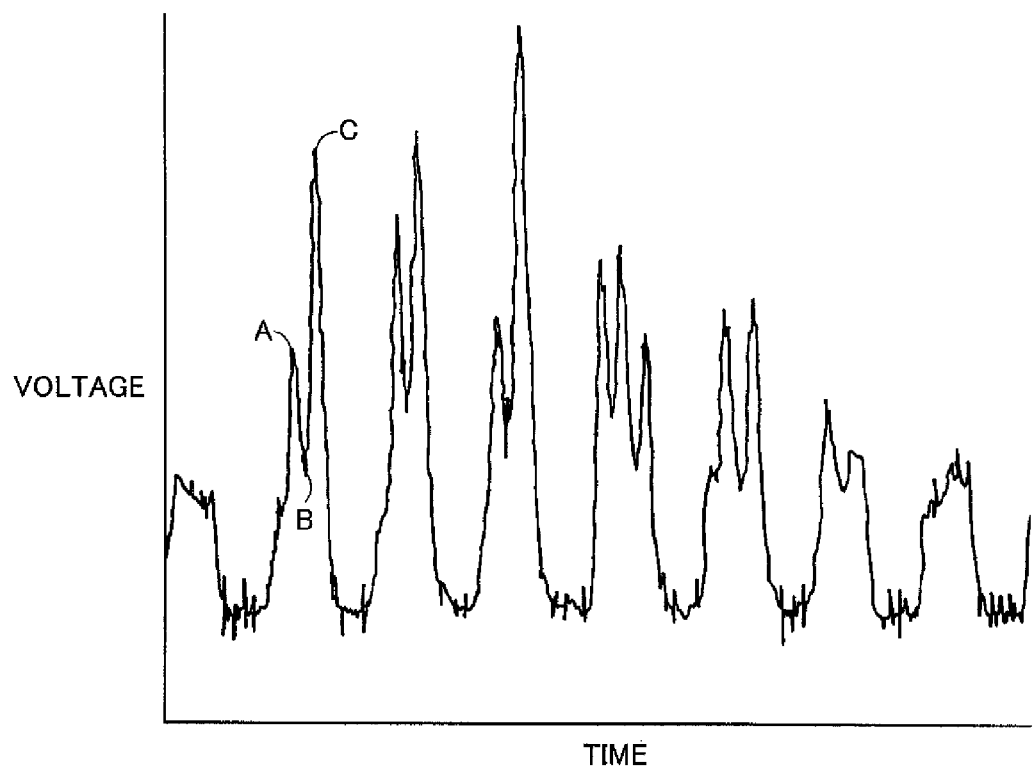
FIG. 7 is a waveform chart showing a signal waveform obtained via a cutting tool when a connection failure occurs in the contact member in the hand piece according to the first embodiment of the present invention.
Figure 8:
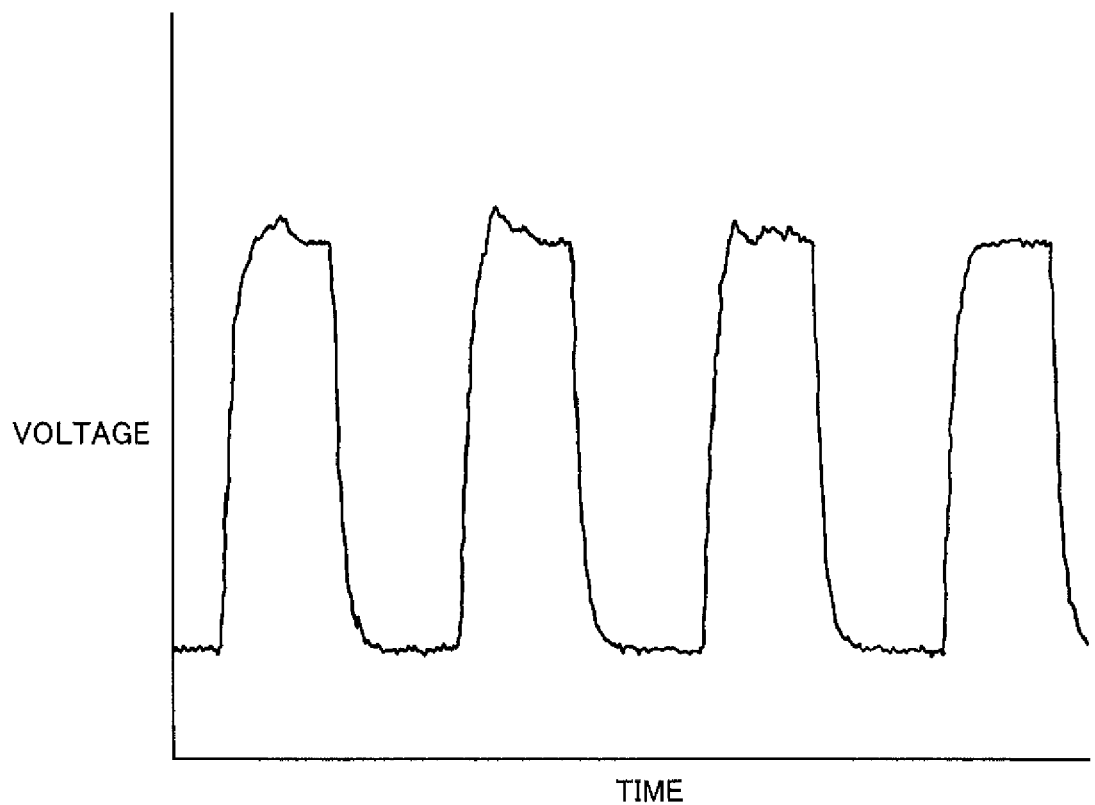
FIG. 8 is a waveform chart showing a signal waveform obtained via the cutting tool when a connection failure does not occur in the contact member in the hand piece according to the first embodiment of the present invention.

Here, FIG. 7 is a waveform chart showing a signal waveform obtained via cutting tool 5 when the connection failure occurs in the contact member in hand piece 1 according to the first embodiment of the present invention. FIG. 8 is a waveform chart showing a signal waveform obtained via cutting tool 5 when the connection failure does not occur in the contact member in hand piece 1 according to the first embodiment of the present invention. It should be noted that horizontal axes in FIGS. 7 and 8 show time, while vertical axes show voltage.

Since the signal waveform as shown in FIG. 7 is obtained via cutting tool 5 by inputting an input signal of rectangular wave for about eight cycles to conductive body 85 of hand piece 1, the waveform includes eight large protrusions corresponding to the input signal of rectangular waveform for about eight cycles. In the signal waveform as shown in FIG. 7, respective convex waveforms change greatly since the connection failure occurs in the contact members. Specifically, in the second left convex waveform of the signal waveforms as shown in FIG. 7, the number of changes of the increasing or decreasing directions of the signal values is three, namely a point A where an increasing direction of the signal value changes to a decreasing direction, a point B where a decreasing direction of the signal value changes to an increasing direction, and a point C where an increasing direction of the signal value changes to a decreasing direction.

Since the signal waveform as shown in FIG. 8 is obtained via cutting tool 5 by inputting an input signal of rectangular wave for about four cycles to conductive body 85 of hand piece 1, the waveform includes four large protrusions corresponding to the input signal of rectangular waveform for about four cycles. In the signal waveform as shown in FIG. 8, respective convex waveforms almost do not change since the connection failure does not occur in the contact members. Namely, in the signal waveform as shown in FIG. 8, for example, greater than or equal to 10% of the signal values with respect to the average value of the signal values per unit time (for a half cycle of the input signal) do not increase or decrease.

Next, connection failure detector 121 determines whether or not the number of changes of the increasing or decreasing directions counted in step S53 is greater than or equal to three (step S54). If the number of changes of the increasing or decreasing directions counted in step S53 is less than three (step S54: NO), connection failure detector 121 determines that the connection failure does not occur in electrode pieces 38, 38 as the contact members, returns a process to step S51, and continues to monitor the connection failure of the contact members while cutting tool 5 is in the root canal of the tooth.

If the number of changes of the increasing or decreasing directions counted in step S53 is greater than or equal to three (step S54: YES), connection failure detector 121 determines that the connection failure occurs in electrode pieces 38, 38 as the contact members and notifier 17 notifies the user of the detection of the connection failure (step S55). Root canal treating device 100 completes operation for monitoring the connection failure of the contact members after step S55.

Figure 9A:
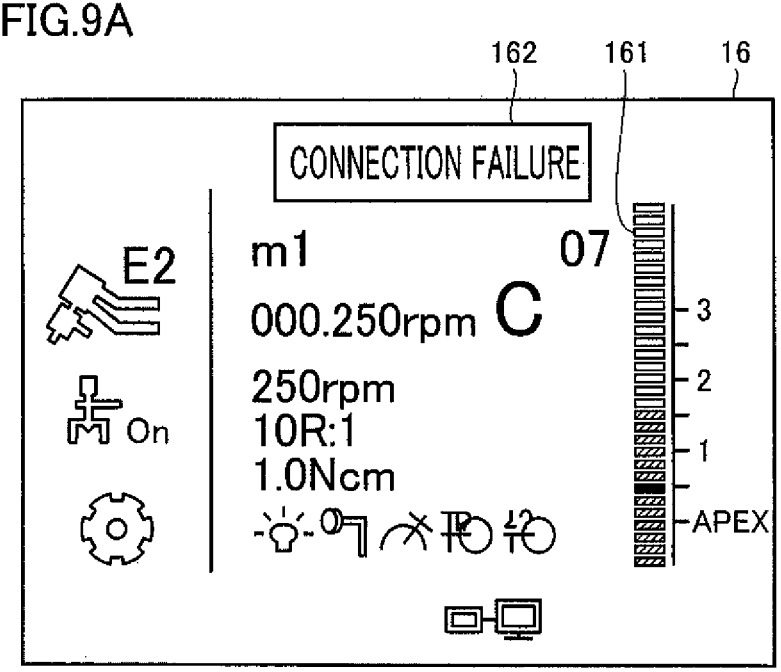
FIG. 9A is a schematic diagram showing a display screen shown by a display unit of the root canal treating device according to the first embodiment of the present invention.
Figure 9B:
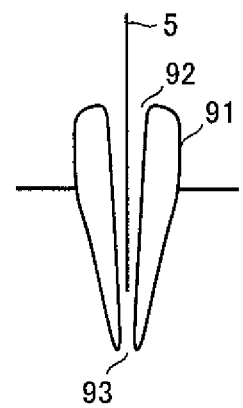
FIG. 9B is a schematic diagram showing a positional relationship of the cutting tool of the root canal treating device according to the first embodiment of the present invention in a root canal of a tooth.

Here, FIG. 9A is a schematic diagram showing a display screen shown by display unit 16 of root canal treating device 100 according to the first embodiment of the present invention. FIG. 9B is a schematic diagram showing a positional relationship of cutting tool 5 of root canal treating device 100 according to the first embodiment of the present invention in the root canal of the tooth. The display screen as shown in FIG. 9A shows each types of information (for example, the number of rotations of cutting tool) of root canal treating device 100, and includes a display indicator 161 showing a position of the tip end of cutting tool 5 in the root canal by lighting display dots based on a value of impedance between cutting tool 5 and mouth electrode 19a. Display indicator 161 corresponds to a position of cutting tool 5 in a root canal 92 of a tooth 91 as shown in FIG. 9B. The display dots shown in white show a substantial amount of insertion of cutting tool 5 in the root canal, while display dots shown in black show a gauge of reference position to switch driving of micro motor 7 from normal rotation to stop, reverse, or speed reduction. A position of the gauge "APEX" shows a position of a root apex 93 of tooth 91 and hatched display dots show a portion of the root canal in which cutting tool 5 is not yet inserted on root apex 93 side with respect to the tip end of cutting tool 5. Accordingly, when the display dots shown in white reach root apex 93 position (gauge "APEX"), or when the display dots shown in white reach the reference position, a distance from the tip end of cutting tool 5 to an opening of the root canal is regarded as a distance from root apex 93 position to the root canal opening, namely the root canal length.

Also, on a display screen as shown in FIG. 9A, display unit 16 can display notification information ("connection failure") 162 to notify the user of the connection failure of the contact members based on the detection result of connection failure detector 121. In other words, in root canal treating device 100, when the signal waveform as shown in FIG. 7 is obtained, connection failure detector 121 determines the connection failure of contact members and display notification information 162 on display unit 16 for notifier 17 to notify the user of the connection failure of the contact members.

As described above, since root canal treating device 100 according to the first embodiment of the present invention detects the connection failure of the contact members based on the response to the input signal by connection failure detector 121, the connection failure due to wear of the contact members can be easily detected in a case where the contact members are provided out of head unit 2 as well as a case where the contact members are provided in head unit 2 such that an appearance cannot be viewed. Further, in root canal treating device 100 according to the first embodiment of the present invention, even when a film of an insulator that cannot be viewed is formed on a surface of the contact members to cause a connection failure, the connection failure of the contact members can be easily detected. Moreover, in root canal treating device 100 according to the first embodiment of the present invention, notifier 17 notifies the user of the detection of the connection failure based on the detection result of connection failure detector 121 to urge the user to notice wear of the contact members and exchange the contact members.

Furthermore, in root canal treating device 100 according to the first embodiment of the present invention, since connection failure detector 121 detects the connection failure of the contact members according to the number of changes of increasing or decreasing directions of signal values of the signal waveform per unit time as a response to an input signal, the connection failure of the contact members can be detected without being effected by a change of the response to the input signal caused by moving cutting tool 5 by the user. It should be noted that it is not necessary for connection failure detector 121 to count the number of changes of the increasing or decreasing directions of the signal value as determination reference to detect the connection failure of the contact members, and a change of the signal waveform can be determination reference to detect the connection failure of the contact members as a response to the input signal. For example, connection failure detector 121 can determine the connection failure of the contact members when the signal value is increased (or decreased) per unit time by greater than or equal to 10% with respect to an average value of the signal values per unit time.

Further, the response to the input signal obtained via cutting tool 5 is not limited to a signal obtained by controller 11 via cutting tool 5, and may be a signal resulted from computing the obtained signal by controller 11. For example, the response to the input signal obtained via cutting tool 5 may be a signal computed by controller 11 to be displayed on a display indicator 161 of display unit 16. That is, when a rate of change of display dots on display indicator 161 is greater than or equal to the rate of change caused by moving cutting tool 5 by the user, connection failure detector 121 can determine the connection failure of the contact members.

Moreover, in root canal treating device 100 according to the first embodiment of the present invention, the operation of notifier 17 is not limited to a case of displaying notification information 162 of a state of the connection failure by displays such as "Connection Failure" and "Error", and notifier 17 may notify the user of information in that the contact members wears out by displays such as "Contact Member Wears" and "Exchange Contact Member". Thereby, root canal treating device 100 can directly urge the user to exchange the contact members due to wear of the contact members.

Furthermore, in dental treating device 100 according to the first embodiment of the present invention, since connection failure detector 121 uses a measurement signal as the input signal, it is not necessary to generate an electric signal separately as the input signal for detecting the connection failure of the contact members.

In the first embodiment of the present invention, a case of root canal treating device 100 is described, but a dental treating apparatus using high-frequency wave or a dental treating apparatus for implant may be used as long as the dental treating apparatus has contact members electrically connected to cutting tool 5 driven in a rotation direction or a vertical direction or a holder holding cutting tool 5.

(Second Embodiment)

A dental treating apparatus according to a second embodiment of the present invention is also a root canal treating device including a root canal enlarging and root canal length measuring system into which a dental hand piece for treatment on a root canal is incorporated. The dental treatment apparatus according to the present invention is, however, not limited to the root canal treating device, and can be applied to a dental treating apparatus with a similar configuration.

It should be noted that the configuration of the root canal treating device according to the second embodiment of the present invention is the same as the configuration of the root canal treating device according to the first embodiment, and thus the same reference numeral is assigned to the same component and detailed description is not repeated.

In root canal treating device 100 according to the second embodiment of the present invention, controller 11 measures accumulated driving time from a time when the contact members are exchanged, and connection failure detector 121 determines the connection failure of the contact members in consideration of the accumulated driving time.

Figure 10:
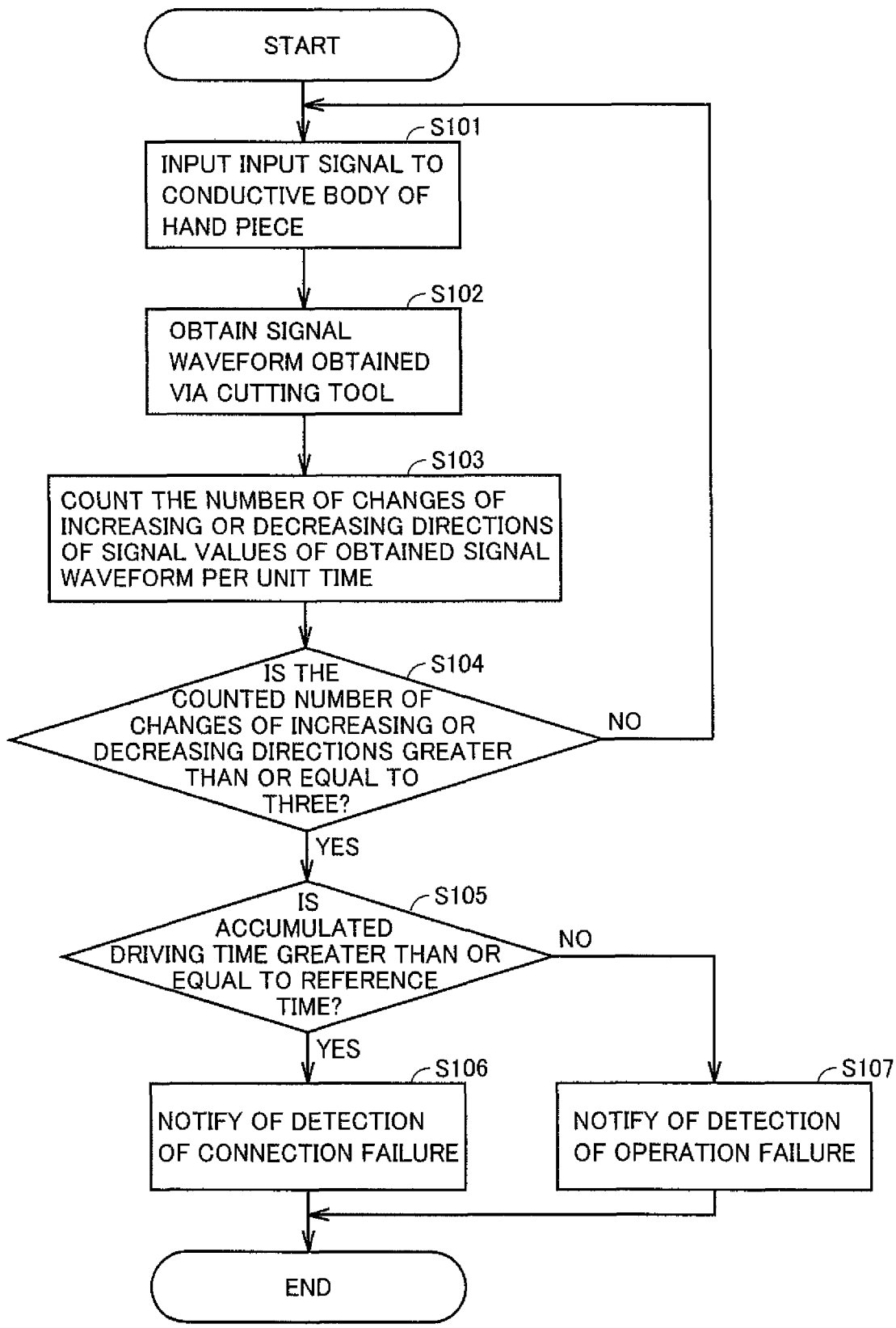
FIG. 10 is a flowchart showing operations of a root canal treating device according to a second embodiment of the present invention.

Specifically, operations of root canal treating device 100 according to the second embodiment of the present invention for determining the connection failure of the contact members are disclosed. FIG. 10 is a flowchart showing operations of root canal treating device 100 according to the second embodiment of the present invention.

First, connection failure detector 121 applies an input signal for measuring the root canal length from root canal length measuring circuit 12, i.e., an input signal of frequency of 8 kHz to conductive body 85 of hand piece 1 (step S101).

Next, connection failure detector 121 applies an input signal to conductive body 85 of hand piece 1 to obtain a signal waveform obtained via cutting tool 5 (step S102).

Next, connection failure detector 121 counts the number of changes of increasing or decreasing directions of signal values of the obtained signal waveform per unit time (step S103).

Next, connection failure detector 121 determines whether or not the number of changes of the increasing or decreasing directions counted in step S103 is greater than or equal to three (step S104). If the number of changes of the increasing or decreasing directions counted in step S103 is less than three (step S104: NO), connection failure detector 121 determines that the connection failure does not occur in electrode pieces 38, 38 as the contact members, returns a process to step S101, and continues to monitor the connection failure of the contact members while cutting tool 5 is in the root canal of the tooth.

If the number of changes of the increasing or decreasing directions counted in step S103 is greater than or equal to three (step S104: YES), connection failure detector 121 determines whether or not accumulate driving time measured by controller 11 is greater than or equal to predetermined reference time (step S105). If the accumulated driving time from a time when electrode pieces 38, 38 as the contact members are exchanged is short, for example a few or a few dozens of hours, it cannot be generally considered that the contact members wear out. Accordingly, even in a case where the number of changes of the increasing or decreasing directions counted in step S103 is greater than or equal to three, if the accumulated driving time is less than the reference time (e.g., 1,000 hours), connection failure detector 121 does not determine that the connection failure occurs in the contact members.

If the accumulated time is less than the reference time (step S105: NO), connection failure detector 121 does not determine that the connection failure is caused by not wear of the contact members but occurrence of operation failure and notifier 17 notifies the user of the detection of the operation failure (step S107).

If the accumulated time is greater than or equal to the reference time (step S105: YES), connection failure detector 121 determines that the connection failure occurs in electrode pieces 38, 38 as the contact members due to wear of the contact members and notifier 17 notifies the user of the detection of the connection failure (step S106). Root canal treating device 100 completes operation for monitoring the connection failure of the contact members after step S106.

As described above, since root canal treating device 100 according to the second embodiment of the present invention detects the connection failure of the contact members when the accumulated driving time is greater than or equal to the predetermined reference time, it is prevented from erroneously determining that the connection failure occurs in the contact members even if the contact members do not wear out.

It should be noted that the accumulated driving time is not limited to a case where it is measured by controller 11, but a timer may be provided separately to measure it. Further, the accumulated driving time is not limited to a case where time when cutting tool 5 is driven to be rotated. If the time when cutting tool 5 is driven to be rotated can be expected to some degrees from a time when root canal treating device 100 is switched on, the accumulated driving time may be the time when root canal treating device 100 is switched to be in an on state. Moreover, measurement of the accumulated driving time is not limited to a case where the time is automatically or manually reset to "0" when the contact members are exchanged, but the accumulated driving time when the contact members are exchanged previously may be stored to measure a difference with respect to current accumulated driving time.

(Third Embodiment)

A dental treating apparatus according to a third embodiment of the present invention is also a root canal treating device including a root canal enlarging and root canal length measuring system into which a dental hand piece for treatment on a root canal is incorporated. The dental treatment apparatus according to the present invention is, however, not limited to the root canal treating device, and can be applied to a dental treating apparatus with a similar configuration.

It should be noted that the configuration of the root canal treating device according to the third embodiment of the present invention is the same as the configuration of the root canal treating device according to the first embodiment, and thus the same reference numeral is assigned to the same component and detailed description is not repeated.

In root canal treating device 100 according to the third embodiment of the present invention, notifier 17 notifies the user of the detection of the connection failure as well as controller 11 stops driving cutting tool 5, reduces driving power, or reverses a direction of driving cutting tool 5 based on a detection result of connection failure detector 121.

Figure 11:
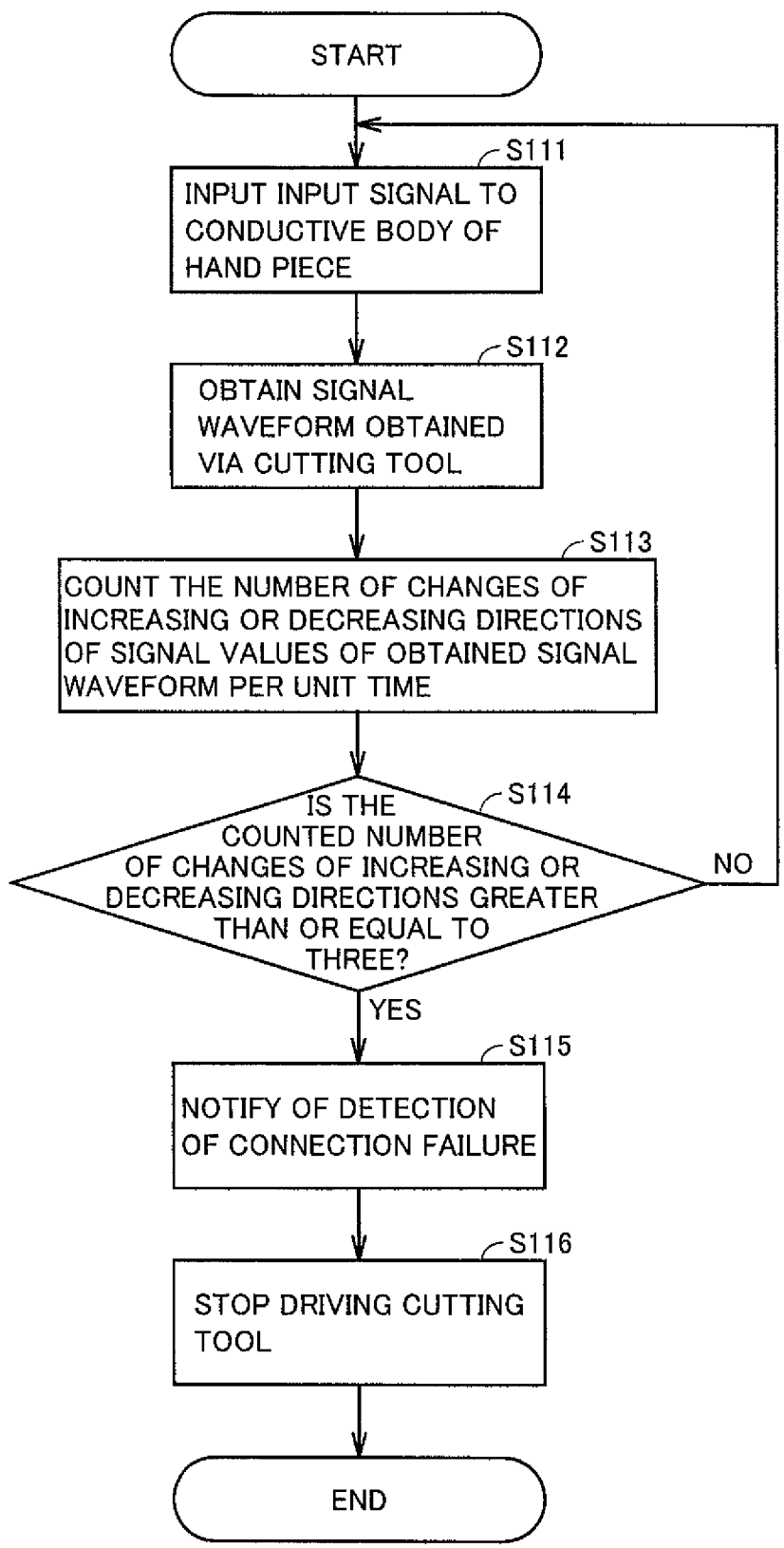
FIG. 11 is a flowchart showing operations of a root canal treating device according to a third embodiment of the present invention.

Specifically, operations of root canal treating device 100 according to the third embodiment of the present invention for determining the connection failure of the contact members are disclosed. FIG. 11 is a flowchart showing the operations of root canal treating device 100 according to the third embodiment of the present invention.

First, connection failure detector 121 applies an input signal for measuring the root canal length from root canal length measuring circuit 12, i.e., an input signal of frequency of 8 kHz to conductive body 85 of hand piece 1 (step S111).

Next, connection failure detector 121 applies an input signal to conductive body 85 of hand piece 1 to obtain a signal waveform obtained via cutting tool 5 (step S112).

Next, connection failure detector 121 counts the number of changes of increasing or decreasing directions of signal values of the obtained signal waveform per unit time (step S113).

Next, connection failure detector 121 determines whether or not the number of changes of the increasing or decreasing directions counted in step S113 is greater than or equal to three (step S114). If the number of changes of the increasing or decreasing directions counted in step S113 is less than three (step S114: NO), connection failure detector 121 determines that the connection failure does not occur in electrode pieces 38, 38 as the contact members, returns a process to step S111, and continues to monitor the connection failure of the contact members while cutting tool 5 is in the root canal of the tooth.

If the number of changes of the increasing or decreasing directions counted in step S113 is greater than or equal to three (step S114: YES), connection failure detector 121 determines that the connection failure occurs in electrode pieces 38, 38 as the contact members and notifier 17 notifies the user of the detection of the connection failure (step S115).

Next, controller 11 stops driving cutting tool 5 based on the detection result of connection failure detector 121 (step S116). That is, if the connection failure occurs in the contact members, root canal treating device 100 cannot measure the root canal length with high accuracy so that controller 11 stops driving cutting tool 5 for more safety. It should be noted that controller 11 may not stop driving cutting tool 5 but may reduce driving force of cutting tool 5, or may reverse a driving direction of cutting tool 5.

Root canal treating device 100 completes operation for monitoring the connection failure of the contact members after step S116.

As described above, in root canal treating device 100 according to the third embodiment of the present invention, when connection failure detector 121 detects that the connection failure occurs in the contact members, controller 11 stops driving, reduces driving force or reverses a driving direction of cutting tool 5. Therefore, not only notifying the user of a fact that the connection failure occurs in the contact members and the root canal length cannot be measured with high accuracy, root canal treating device 100 may be used more safely.

In root canal treating device 100 according to the third embodiment of the present invention, a case is described where after notifier 17 notifies the user of the detection of the connection failure, controller 11 stops driving, reduces driving force, or reverses a driving direction of cutting tool 5, but the present invention is not limited to this case. Notifier 17 may notify the user of the detection of the connection failure after controller 11 stops driving, reduces driving force, or reverses a driving direction of cutting tool 5.

Further, in root canal treating device 100 according to the third embodiment of the present invention, a case is described where controller 11 performs any one of operations of stopping driving, reducing driving force, or reversing a driving direction of cutting tool 5, but the present invention is not limited to this case. A plurality of the operations may be combined with each other. For example, controller 11 may reduce driving force of cutting tool 5 based on detection result of connection failure detector 121, and thereafter reverse a driving direction of cutting tool 5, and then stop driving cutting tool 5.

Moreover, a step of performing, by controller 11, operations such as stopping driving cutting tool 5 based on the detection result of connection failure detector 121 may be performed after the steps of S106 and S107 in the flowchart as shown in FIG. 10 according to the second embodiment.

(Fourth Embodiment)

A dental treating apparatus according to a fourth embodiment of the present invention is also a root canal treating device including a root canal enlarging and root canal length measuring system into which a dental hand piece for treatment on a root canal is incorporated. The dental treatment apparatus according to the present invention is, however, not limited to the root canal treating device, and can be applied to a dental treating apparatus with a similar configuration.

It should be noted that the configuration of the root canal treating device according to the fourth embodiment of the present invention is the same as the configuration of the root canal treating device according to the first embodiment, and thus the same reference numeral is assigned to the same component and detailed description is not repeated.

In root canal treating device 100 according to the fourth embodiment of the present invention, contact members are not disposed in head unit 2 but disposed out of head unit 2.

Figure 12:
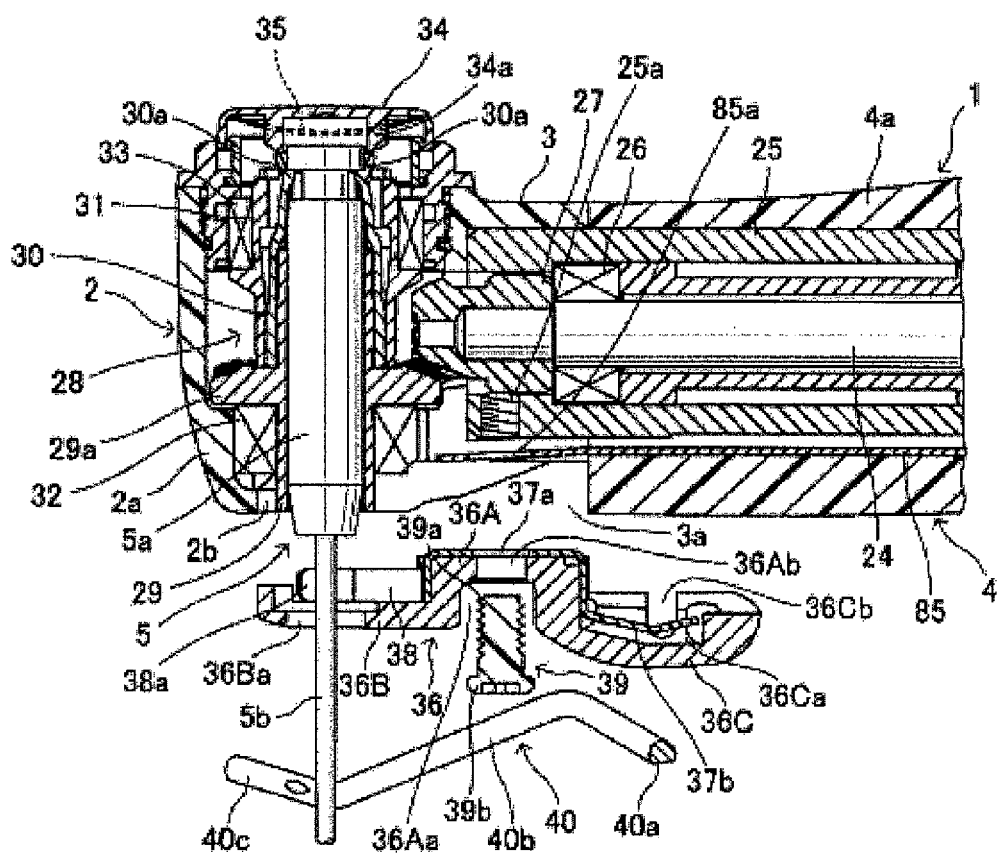
FIG. 12 is a cross-sectional view illustrating the configuration of a tip end of a hand piece according to a fourth embodiment of the present invention.

FIG. 12 is a cross-sectional view illustrating the configuration of a tip end of hand piece 1 according to the fourth embodiment of the present invention.

In hand piece 1 as shown in FIG. 12, another electrode piece 40 in an electrically conductive state with respect to contact piece 37 is provided on cover member 36 such that this electrode piece 40 contacts with cutting operation part 5b of cutting tool 5. That is, cover member 36 further includes a third part 36C extending from first part 36A opposite to second part 36B (on grip 4 side). Third part 36C includes a concave part 36Ca contacting with a lower surface of grip 4 in the vicinity of contact part with neck unit 3 and defines a hollow between third part 36C and the lower surface. Further, in contact piece 37, a tongue piece 37b facing an inside of concave part 36Ca further extends and tongue piece 37b is formed to include spring property to be elastically deformed in a vertical direction. In each of lateral walls of concave part 36Ca, a cutout 36Cb is formed.

Electrode piece 40 is formed by flexing a conductive wire member. Electrode piece 40 is configured by an axis unit 40a, a pair of sandwiching bars 40b, 40b flexed at both ends of axis unit 40a at acute angles so as to approach with respect to each other, and a pair of guide bars 40c, 40c from tip ends of sandwiching bars 40b, 40b apart to each other. Axis unit 40a is fit into cutouts 36Cb, 36Cb from above to cross third part 36C (perpendicular to an axis of grip 4). Electrode piece 40 is supported such that axis unit 40a is hung on third part 36C, and sandwiching bars 40b, 40b and guide bars 40c, 40c are positioned below cover member 36 and installed on cover member 36 to be oriented to a tip end of second part 36B. Cover member 36 on which electrode piece 40 is installed in a manner as described above is installed on hand piece 1 by engaging stopper 39 with female thread 25a so that first part 36A is stored in concave part 3a of neck unit 3 and second part 36B is stored in cutout 2b of head unit 2, respectively.

Axis unit 40a of electrode piece 40 is elastically sandwiched by tongue piece 37b of contact piece 37 and a lower surface of housing 4a of grip 4. Thereby, axis unit 40a and tongue piece 37b contact to each other so that both of them are in an electrically conductive state. In particular, since tongue piece 37b includes spring property, tongue piece 37b include biasing elasticity in an upper direction to elastically contact with axis unit 40a so as to stably maintain the electrically conductive state. Further, since a portion of axis unit 40a contacting with tongue piece 37b is cut to have a flat surface, surfaces of both of them contact with each other to be in an excellent electrically conductive state.

As guide bars 40c, 40c on the tip end side are pressed to be extended so that guide bars 40c, 40c sandwich cutting operation part 5b of cutting tool 5, sandwiching bars 40b, 40b are pressed to be extended so that cutting operation part 5b passes through between sandwiching bars 40b, 40b. After cutting operation part Sb passes through, sandwiching bars 40b, 40b contact and sandwich cutting operation part 5b by being effected by returning elasticity thereof.

When measuring the root canal length, cutting operation part 5b of cutting tool 5 is used as one of the electrodes of the root canal length measuring circuit to be in an electrically conductive state with respect to signal lead 8 as one of the electrodes of the root canal length measuring circuit via electrode piece 40, tongue piece 37b, contact piece 37, conductive body 85, lead 83, and the like.

As described above and shown in FIG. 12, in root canal treating device 100 according to the fourth embodiment of the present invention, electrode piece 40 as the contact member is provided out of head unit 2 to obtain a similar advantage.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A dental treating apparatus comprising:
   a head unit having a holder configured for drivably holding a cutting tool;
   a hand piece body connected to said head unit for transmitting power to drive said holder; and
   a controller configured for controlling the driving of said holder, said dental treating apparatus further comprising:
     a conductive body disposed in an inside of said hand piece body for transmitting an electric signal;
     contact members disposed in an inside of said head unit and electrically connecting said holder with said conductive body;
     a connection failure detector configured for applying a predetermined input signal to said conductive body and detecting a connection failure of said contact members; and
     a notifier configured for receiving detection result from said connection failure detector and for notifying a user based on said detection result,
   wherein said connection failure detector comprises a waveform obtainer,
   wherein said waveform obtainer obtains a signal waveform via said holder as a response to said input signal,
   wherein said connection failure detector detects said connection failure based on a change of signal waveform obtained by said waveform obtainer, and
   wherein said connection failure detector is configured to store accumulated driven time for driving said cutting tool after said contact members are exchanged and detects a connection failure of said contact members based on a response to said input signal obtained via said cutting tool when said stored accumulated driven time is greater than or equal to a predetermined period.

2. The dental treating apparatus according to claim 1, wherein said connection failure detector is configured to detect connection failure of said contact members according to the number of changes of increasing or decreasing directions of signal values of said signal waveform per unit time obtained via said cutting tool as the response to said input signal.

3. The dental treating apparatus according to claim 1, wherein said notifier notifies said user of a fact in that said contact members has been worn out by driving said cutting tool based on the detection result of said connection failure detector.

4. The dental treating apparatus according to claim 1, wherein said controller stops driving said cutting tool, reduces driving force or reverses a driving direction of said cutting tool based on the detection result by said connection failure detector.

5. The dental treating apparatus according to claim 1 that measures a root canal length by applying a predetermined measurement signal to said conductive body, wherein said connection failure detector uses said measurement signal as said input signal.

* * * * *